US008895786B2

(12) United States Patent
Orosco et al.

(10) Patent No.: US 8,895,786 B2
(45) Date of Patent: Nov. 25, 2014

(54) PROCESSES FOR INCREASING ALCOHOL PRODUCTION

(75) Inventors: Adam Orosco, Houston, TX (US); Manuel Salado, Seabrook, TX (US); Lincoln Sarager, Houston, TX (US); R. Jay Warner, Houston, TX (US); Trinity Horton, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 430 days.

(21) Appl. No.: 13/197,723

(22) Filed: Aug. 3, 2011

(65) Prior Publication Data

US 2013/0035522 A1 Feb. 7, 2013

(51) Int. Cl.
*C07C 29/12* (2006.01)
*C07C 29/88* (2006.01)
*B01D 3/00* (2006.01)
*C07C 29/149* (2006.01)
*C07C 29/80* (2006.01)
*C07C 51/12* (2006.01)
*B01D 3/14* (2006.01)

(52) U.S. Cl.
CPC .............. *B01D 3/143* (2013.01); *C07C 29/88* (2013.01); *B01D 3/002* (2013.01); *C07C 29/149* (2013.01); *C07C 29/80* (2013.01); *C07C 51/12* (2013.01)
USPC ............ 568/890; 568/881; 568/884; 568/885

(58) Field of Classification Search
None
See application file for complete search history.

(56) References Cited

U.S. PATENT DOCUMENTS

| | | |
|---|---|---|
| 1,939,116 A | 12/1933 | Fuchs |
| 2,607,807 A | 8/1952 | Ford |
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,709,795 A | 1/1973 | Singleton |
| 3,769,329 A | 10/1973 | Knox et al. |
| 3,864,284 A | 2/1975 | Clippinger et al. |
| 3,884,981 A | 5/1975 | Kiff |
| 3,925,490 A | 12/1975 | Reich et al. |
| 3,990,952 A | 11/1976 | Katzen et al. |
| 4,008,131 A | 2/1977 | Price |
| 4,039,395 A | 8/1977 | Eby |
| 4,107,002 A | 8/1978 | Eck et al. |
| 4,126,539 A | 11/1978 | Derr, Jr. et al. |
| 4,149,940 A | 4/1979 | Pinto |
| 4,262,154 A | 4/1981 | Gane et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,328,375 A | 5/1982 | Barlow |
| 4,338,221 A | 7/1982 | Qualeatti |
| 4,352,940 A | 10/1982 | Adelman et al. |
| 4,352,947 A | 10/1982 | Habib et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa et al. |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,451,677 A | 5/1984 | Bradley et al. |
| 4,454,358 A | 6/1984 | Kummer et al. |
| 4,456,775 A | 6/1984 | Travers et al. |
| 4,465,854 A | 8/1984 | Pond et al. |
| 4,471,136 A | 9/1984 | Larkins et al. |
| 4,476,326 A | 10/1984 | Lin et al. |
| 4,480,115 A | 10/1984 | McGinnis |
| 4,481,146 A | 11/1984 | Leupold et al. |
| 4,492,808 A | 1/1985 | Hagen et al. |
| 4,497,967 A | 2/1985 | Wan |
| 4,514,515 A | 4/1985 | Travers et al. |
| 4,514,521 A | 4/1985 | Smith |
| 4,517,391 A | 5/1985 | Schuster et al. |

(Continued)

FOREIGN PATENT DOCUMENTS

| | | |
|---|---|---|
| CA | 1233484 | 3/1988 |
| CN | 1230458 | 10/1999 |

(Continued)

OTHER PUBLICATIONS

Witzeman and Agreda in "Acetic Acid and its Derivatives," Marcel Dekker, NY, 1992, p. 271.

(Continued)

*Primary Examiner* — Sudhakar Katakam

(57) ABSTRACT

A process for reducing ethyl acetate and/or diethyl acetal concentration of a crude ethanol product by hydrolysis is disclosed. A portion of the water is initially separated from the crude ethanol product in a first column residue. Ethyl acetate in the first column distillate is hydrolyzed to form additional ethanol and acetic acid. Product ethanol is recovered in a second distillation column preferably in a side stream and acetic acid is removed in the second column residue.

29 Claims, 3 Drawing Sheets

(56) References Cited

U.S. PATENT DOCUMENTS

| | | |
|---|---|---|
| 4,520,213 A | 5/1985 | Victor |
| 4,541,897 A | 9/1985 | Sommer et al. |
| 4,556,644 A | 12/1985 | Erpenbach et al. |
| 4,569,726 A | 2/1986 | Berg et al. |
| 4,611,085 A | 9/1986 | Kitson |
| 4,626,321 A | 12/1986 | Grethlein et al. |
| 4,626,604 A | 12/1986 | Hiles et al. |
| 4,628,130 A | 12/1986 | Bournonville et al. |
| 4,629,711 A | 12/1986 | Erpenbach et al. |
| 4,664,753 A | 5/1987 | Erpenbach et al. |
| 4,678,543 A | 7/1987 | Houben et al. |
| 4,692,218 A | 9/1987 | Houben et al. |
| 4,737,318 A | 4/1988 | Ichino et al. |
| 4,751,334 A | 6/1988 | Turner et al. |
| 4,758,600 A | 7/1988 | Arimitsu et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,837,367 A | 6/1989 | Gustafson et al. |
| 4,837,368 A | 6/1989 | Gustafson et al. |
| 4,842,693 A | 6/1989 | Wheldon |
| 4,876,402 A | 10/1989 | Logsdon et al. |
| 4,886,905 A | 12/1989 | Larkins et al. |
| 4,908,477 A | 3/1990 | Hartmann et al. |
| 4,961,826 A | 10/1990 | Grethlein et al. |
| 4,978,778 A | 12/1990 | Isshiki et al. |
| 4,985,572 A | 1/1991 | Kitson et al. |
| 4,990,655 A | 2/1991 | Kitson et al. |
| 4,992,582 A | 2/1991 | Ruppert et al. |
| 4,994,608 A | 2/1991 | Torrence et al. |
| 5,001,259 A | 3/1991 | Smith et al. |
| 5,004,845 A | 4/1991 | Bradley et al. |
| 5,008,235 A | 4/1991 | Wegman et al. |
| 5,026,908 A | 6/1991 | Smith et al. |
| 5,035,776 A | 7/1991 | Knapp |
| 5,047,592 A | 9/1991 | Carpenter |
| 5,061,671 A | 10/1991 | Kitson et al. |
| 5,070,016 A | 12/1991 | Hallberg |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,185,476 A | 2/1993 | Gustafson |
| 5,185,481 A | 2/1993 | Muto et al. |
| 5,196,601 A | 3/1993 | Kitsuki et al. |
| 5,198,592 A | 3/1993 | Van Beijnum et al. |
| 5,215,902 A | 6/1993 | Tedder |
| 5,220,020 A | 6/1993 | Buchwald et al. |
| 5,227,141 A | 7/1993 | Kim et al. |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe et al. |
| 5,254,758 A | 10/1993 | Hiles et al. |
| 5,300,685 A | 4/1994 | Scates et al. |
| 5,334,751 A | 8/1994 | Lemanski et al. |
| 5,348,625 A | 9/1994 | Berg |
| 5,362,918 A | 11/1994 | Aizawa et al. |
| 5,399,752 A | 3/1995 | Okrasinski et al. |
| 5,403,962 A | 4/1995 | Schneider et al. |
| 5,414,161 A | 5/1995 | Uhm et al. |
| 5,415,741 A | 5/1995 | Berg |
| 5,416,237 A | 5/1995 | Aubigne et al. |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,476,974 A | 12/1995 | Moore et al. |
| 5,480,665 A | 1/1996 | Smith |
| 5,488,185 A | 1/1996 | Ramachandran et al. |
| 5,502,094 A | 3/1996 | Moore et al. |
| 5,502,248 A | 3/1996 | Funk et al. |
| 5,527,969 A | 6/1996 | Kaufhold et al. |
| 5,567,765 A | 10/1996 | Moore et al. |
| RE35,377 E | 11/1996 | Steinberg et al. |
| 5,599,976 A | 2/1997 | Scates et al. |
| 5,658,962 A | 8/1997 | Moore et al. |
| 5,696,284 A | 12/1997 | Baker et al. |
| 5,731,252 A | 3/1998 | Warner et al. |
| 5,747,486 A | 5/1998 | Sohda et al. |
| 5,762,765 A | 6/1998 | Berg |
| 5,770,761 A | 6/1998 | Lin et al. |
| 5,770,770 A | 6/1998 | Kim et al. |
| 5,800,681 A | 9/1998 | Berg |
| 5,821,111 A | 10/1998 | Grady et al. |
| 5,831,133 A | 11/1998 | Mimoun |
| 5,861,530 A | 1/1999 | Atkins et al. |
| 5,877,347 A | 3/1999 | Ditzel et al. |
| 5,877,348 A | 3/1999 | Ditzel et al. |
| 5,883,295 A | 3/1999 | Sunley et al. |
| 5,932,764 A | 8/1999 | Morris et al. |
| 5,942,460 A | 8/1999 | Garland et al. |
| 5,955,397 A | 9/1999 | Didillon et al. |
| 5,973,193 A | 10/1999 | Crane et al. |
| 5,977,010 A | 11/1999 | Roberts et al. |
| 5,993,610 A | 11/1999 | Berg |
| 5,998,658 A | 12/1999 | Wu et al. |
| 6,024,176 A | 2/2000 | Moore et al. |
| 6,040,474 A | 3/2000 | Jobson et al. |
| 6,046,127 A | 4/2000 | Mimoun |
| 6,049,008 A | 4/2000 | Roberts et al. |
| 6,093,845 A | 7/2000 | Van Acker et al. |
| 6,121,497 A | 9/2000 | Murphy |
| 6,121,498 A | 9/2000 | Tustin et al. |
| 6,140,535 A | 10/2000 | Williams |
| 6,143,930 A | 11/2000 | Singh et al. |
| 6,204,299 B1 | 3/2001 | Moore et al. |
| 6,214,253 B1 | 4/2001 | Moore et al. |
| 6,232,352 B1 | 5/2001 | Vidalin |
| 6,294,703 B1 | 9/2001 | Hara et al. |
| 6,326,515 B1 | 12/2001 | Clode et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,458,996 B1 | 10/2002 | Muskett |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,555 B2 | 10/2002 | Choudary et al. |
| 6,472,572 B1 | 10/2002 | Zhou et al. |
| 6,486,366 B1 | 11/2002 | Ostgard et al. |
| 6,486,368 B1 | 11/2002 | Zhou et al. |
| 6,491,983 B2 | 12/2002 | Moore et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,525,230 B2 | 2/2003 | Grosso |
| 6,552,220 B1 | 4/2003 | Obana et al. |
| 6,627,770 B1 | 9/2003 | Cheung et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,713,655 B2 | 3/2004 | Yilmaz et al. |
| 6,723,886 B2 | 4/2004 | Allison et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,863,211 B2 | 3/2005 | Moore et al. |
| 6,867,164 B2 | 3/2005 | Obana et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,019,182 B2 | 3/2006 | Grosso |
| 7,074,603 B2 | 7/2006 | Verser et al. |
| 7,084,312 B1 | 8/2006 | Huber et al. |
| 7,091,155 B2 | 8/2006 | Inui et al. |
| 7,115,772 B2 | 10/2006 | Picard et al. |

(56) References Cited

U.S. PATENT DOCUMENTS

| | | |
|---|---|---|
| 7,148,390 B2 | 12/2006 | Zhou et al. |
| 7,161,050 B2 | 1/2007 | Sherman et al. |
| 7,208,624 B2 | 4/2007 | Scates et al. |
| 7,223,886 B2 | 5/2007 | Scates et al. |
| 7,230,150 B2 | 6/2007 | Grosso et al. |
| 7,297,236 B1 | 11/2007 | Vander Griend et al. |
| 7,351,559 B2 | 4/2008 | Verser et al. |
| 7,361,794 B2 | 4/2008 | Grosso |
| 7,375,049 B2 | 5/2008 | Hayes et al. |
| 7,399,892 B2 | 7/2008 | Rix et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,652,167 B2 | 1/2010 | Miller et al. |
| 7,667,068 B2 | 2/2010 | Miller et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,725,657 B2 | 5/2010 | Hasenplaugh et al. |
| 7,732,173 B2 | 6/2010 | Mairal et al. |
| 7,744,727 B2 | 6/2010 | Blum et al. |
| 7,820,852 B2 | 10/2010 | Johnston et al. |
| 7,834,223 B2 | 11/2010 | Atkins et al. |
| 7,838,708 B2 | 11/2010 | Sherman et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,906,680 B2 | 3/2011 | Scates et al. |
| 7,947,746 B2 | 5/2011 | Daniel et al. |
| 7,964,379 B2 | 6/2011 | Verser et al. |
| 7,994,368 B2 | 8/2011 | Johnston et al. |
| 8,071,821 B2 | 12/2011 | Johnston et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0004057 A1 | 1/2003 | Yamaguchi et al. |
| 2003/0013908 A1 | 1/2003 | Horan et al. |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0114719 A1 | 6/2003 | Fischer et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0009614 A1 | 1/2004 | Ahn et al. |
| 2004/0063184 A1 | 4/2004 | Grichko |
| 2004/0152915 A1 | 8/2004 | Fujita et al. |
| 2004/0232049 A1 | 11/2004 | Dath et al. |
| 2004/0242917 A1 | 12/2004 | Inui et al. |
| 2004/0267074 A1 | 12/2004 | Grosso et al. |
| 2005/0043572 A1 | 2/2005 | Grosso |
| 2005/0192468 A1 | 9/2005 | Sherman et al. |
| 2005/0209328 A1 | 9/2005 | Allgood et al. |
| 2005/0214408 A1 | 9/2005 | Pilkington et al. |
| 2006/0019360 A1 | 1/2006 | Verser et al. |
| 2006/0127999 A1 | 6/2006 | Verser et al. |
| 2006/0224013 A1 | 10/2006 | Inui et al. |
| 2006/0247466 A1 | 11/2006 | Zinobile et al. |
| 2006/0252956 A1 | 11/2006 | Miller et al. |
| 2007/0031954 A1 | 2/2007 | Mairal et al. |
| 2007/0106246 A1 | 5/2007 | Modesitt |
| 2007/0144886 A1 | 6/2007 | Sylvester et al. |
| 2007/0265360 A1 | 11/2007 | Luo et al. |
| 2007/0270511 A1 | 11/2007 | Melnichuk et al. |
| 2008/0103335 A1 | 5/2008 | Scates et al. |
| 2008/0135396 A1 | 6/2008 | Blum |
| 2008/0187472 A1 | 8/2008 | Ahn et al. |
| 2008/0193989 A1 | 8/2008 | Verser et al. |
| 2008/0207953 A1 | 8/2008 | Houssin et al. |
| 2008/0257784 A1 | 10/2008 | Dath et al. |
| 2008/0269518 A1 | 10/2008 | Scates et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0099389 A1 | 4/2009 | Shaver |
| 2009/0166172 A1 | 7/2009 | Casey et al. |
| 2009/0221725 A1 | 9/2009 | Chornet et al. |
| 2009/0264285 A1 | 10/2009 | Luo et al. |
| 2009/0270651 A1 | 10/2009 | Zinobile et al. |
| 2009/0281354 A1 | 11/2009 | Mariansky et al. |
| 2009/0299092 A1 | 12/2009 | Beavis et al. |
| 2009/0318573 A1 | 12/2009 | Stites et al. |
| 2009/0326080 A1 | 12/2009 | Chornet et al. |
| 2009/0326268 A1 | 12/2009 | Hanes et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0041919 A1 | 2/2010 | Wu et al. |
| 2010/0063319 A1 | 3/2010 | Brtko et al. |
| 2010/0069515 A1 | 3/2010 | Tirtowidjojo et al. |
| 2010/0080736 A1 | 4/2010 | Hassan et al. |
| 2010/0121114 A1 | 5/2010 | Johnston et al. |
| 2010/0121119 A1 | 5/2010 | Sherman et al. |
| 2010/0137630 A1 | 6/2010 | Garton et al. |
| 2010/0145097 A1 | 6/2010 | Brtko et al. |
| 2010/0168493 A1 | 7/2010 | Le Peltier et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0204512 A1 | 8/2010 | Kimmich et al. |
| 2010/0249479 A1 | 9/2010 | Berg-Slot et al. |
| 2010/0261800 A1 | 10/2010 | Daniel et al. |
| 2010/0273229 A1 | 10/2010 | Verser et al. |
| 2010/0311138 A1 | 12/2010 | Padgett |
| 2011/0004033 A1 | 1/2011 | Johnston et al. |
| 2011/0004034 A1 | 1/2011 | Daniel et al. |
| 2011/0034741 A1 | 2/2011 | Sherman et al. |
| 2011/0046421 A1* | 2/2011 | Daniel et al. .............. 568/885 |
| 2011/0082322 A1 | 4/2011 | Jevtic et al. |
| 2011/0098501 A1 | 4/2011 | Johnston et al. |
| 2011/0185628 A1 | 8/2011 | Johnston et al. |
| 2011/0190547 A1 | 8/2011 | Jevtic et al. |
| 2011/0190548 A1 | 8/2011 | Jevtic et al. |
| 2011/0190552 A1 | 8/2011 | Powell et al. |
| 2011/0224462 A1 | 9/2011 | Ditzel et al. |
| 2011/0263911 A1 | 10/2011 | Johnston et al. |
| 2011/0275861 A1 | 11/2011 | Johnston et al. |
| 2011/0275862 A1 | 11/2011 | Johnston et al. |
| 2012/0010438 A1 | 1/2012 | Lee et al. |
| 2012/0010445 A1 | 1/2012 | Johnston et al. |

FOREIGN PATENT DOCUMENTS

| | | |
|---|---|---|
| CN | 1944373 | 4/2007 |
| CN | 1944374 | 4/2007 |
| CN | 101665424 | 3/2010 |
| CN | 201768393 | 3/2011 |
| CN | 102228831 | 11/2011 |
| CN | 102229520 | 11/2011 |
| DE | 241590 | 12/1986 |
| DE | 60025239 | 6/2006 |
| EP | 0056488 | 7/1982 |
| EP | 0087870 | 9/1983 |
| EP | 0104197 | 4/1984 |
| EP | 0137749 | 4/1985 |
| EP | 0167300 | 1/1986 |
| EP | 0175558 | 3/1986 |

(56) References Cited

FOREIGN PATENT DOCUMENTS

| | | |
|---|---|---|
| EP | 0192587 | 8/1986 |
| EP | 0198682 | 10/1986 |
| EP | 0285420 | 10/1988 |
| EP | 0285786 | 10/1988 |
| EP | 0400904 | 5/1990 |
| EP | 0372847 | 6/1990 |
| EP | 0456647 | 11/1991 |
| EP | 0535825 | 5/1996 |
| EP | 0944572 | 9/1999 |
| EP | 0990638 | 4/2000 |
| EP | 0992482 | 4/2000 |
| EP | 1338587 | 8/2003 |
| EP | 2 060 553 A1 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 2053915 | 2/1981 |
| JP | 60-09454 | 1/1985 |
| JP | 60-25033 | 2/1985 |
| JP | 61-28181 | 2/1986 |
| JP | 02-215790 | 8/1990 |
| JP | 4-193304 | 7/1992 |
| JP | 51-86391 | 7/1993 |
| JP | 6-116182 | 4/1994 |
| JP | 2001-046874 | 2/2001 |
| JP | 2001-157841 | 6/2001 |
| JP | 2005-289936 | 10/2005 |
| KR | 2012 0010763 | 2/2012 |
| WO | WO 82/03854 | 11/1982 |
| WO | WO 83/03409 | 10/1983 |
| WO | WO 98/25876 | 6/1998 |
| WO | WO 02/092541 | 11/2002 |
| WO | WO 2005/102513 | 11/2005 |
| WO | WO 2007/003897 | 1/2007 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/103948 | 8/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/030320 | 3/2010 |
| WO | WO 2010/055285 | 5/2010 |
| WO | WO 2011/053365 | 5/2011 |
| WO | WO 2011/056597 | 5/2011 |
| WO | WO 2011/097193 | 8/2011 |
| WO | WO 2011/097208 | 8/2011 |
| WO | WO 2011/097217 | 8/2011 |
| WO | WO 2011/097219 | 8/2011 |
| WO | WO 2011/140455 | 11/2011 |
| WO | WO 2012/006228 | 1/2012 |
| WO | WO 2012/006388 | 1/2012 |
| WO | WO 2012/006499 | 1/2012 |

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on PT/SiO2 catalysts modified with SnBu4, Studies in Surface Science and Catalysis, 130, 2063-2068.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

International Search Report and Written Opinion mailed Sep. 2, 2011 in corresponding International Application No. PCT/US2011/023276.

Written Opinion mailed May 8, 2012 in corresponding International Application No. PCT/US2011/023276.

International Search Report and Written Opinion mailed on Aug. 11, 2011 in corresponding International Application No. PCT/US2011/023283.

Written Opinion mailed on Jan. 30, 2012 in corresponding International Application No. PCT/US2011/023283.

International Search Report and Written Opinion mailed Sep. 6, 2011 in corresponding International Application No. PCT/US2011/023338.

Invitation to Pay Additional Fees and Partial Search Report mailed May 4, 2011 in corresponding International Application No. PCT/US2011/023283.

International Preliminary Report on Patentability mailed May 18, 2012 in corresponding International Application No. PCT/US2011/023283.

Written Opinion mailed May 16, 2012 in corresponding International Application No. PCT/US2011/023338.

Claus, et al., "Selective Hydrogenolysis of methyl and ethyl acetate in the gas phase on copper and supported Group VIII metal catalysts", Applied Catalysis A, 79, 1991, p. 1-18.

Pallasana et al., "Reaction Paths in the Hydrogenolysis of Acetic Acid to Ethanol over Pd(111), Re(0001), and RdRe Alloys", Journal of Catalysis, 209, Mar. 1, 2002, pp. 289-305.

International Search Report and Written Opinion mailed May 31, 2012 in corresponding International Application No. PCT/US2011/043213.

US Office Action mailed May 3, 2012 in corresponding U.S. Appl. No. 12/833,737.

International Preliminary Report on Patentability mailed Jun. 27, 2012 in corresponding International Application No. PCT/US2011/023276.

International Preliminary Report on Patentability mailed Jul. 5, 2012 in corresponding International Application No. PCT/US2011/023338.

International Search Report and Written Opinion mailed Jun. 11, 2012 in corresponding International Application No. PCT/US2012/020977.

Gursahani et al., "Reaction kinetics measurements and analysis of reaction pathways for conversions of acetic acid, ethanol, and ethyl acetate over silica-supported Pt", Applied Catalysis A: General 222 (2001) 369-392.

Invitation to Pay Fees mailed Mar. 13, 2012 in corresponding International Application No. PCT/US2012/020977.

International Search Report and Written Opinion mailed Mar. 14, 2012 in corresponding International Application No. PCT/US2012/020979.

Pestman et al., Identification of the Active Sites in the Selective Hydrogenation of Acetic Acid to Acetaldehyde on Iron Oxide Catalysts, Journal of Catalysis 174:142-152 (1998).

International Search Report and Written Opinion for PCT/US2011/043310 dated Feb. 23, 2012.

Subramani et al. "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

(56) References Cited

OTHER PUBLICATIONS

Michael Gauβ, et al., Applied Homogeneous Catalysis with Organometallic Compounds: A Comprehensive Handbook in two Volume, Chapter 2.1, p. 27-200, (1st ed., 1996).
Juran et al., "Convert Methanol to Ethanol", Hydrocarbon Processing, Oct. 1985, pp. 85-87.
Zhang et al., "Hydrogenation of Ethyl Acetate to Ethanol over Ni-Based Catalysts Obtained from Ni/Ai Hydrotalcite-Like Compounds", Molecules, 2010, 15, 5139-5152.
International Search Report and Written Opinion mailed Jul. 12, 2012 in corresponding International Application No. PCT/US2012/035166.
Rachmady, Acetic Acid Reduction by H2 on Bimetallic Pt-Fe Catalysts, Journal of Catalysis 209, 87-98, Apr. 1, 2002, Elsevier Science (USA).
J. Jones, et al., "The Cativa™ Process for the Manufacture of Acetic Acid", Platinum Metals Review, vol. 44, No. 3, pp. 94-104 (Jul. 2000).
Hilmen, Separation of Azeotropic Mixtures: Tools for Analysis and Studies on Batch Distillation Operation (Nov. 2000) pp. 17-20.
International Search Report and Written Opinion mailed Jul. 6, 2012 in corresponding International Application No. PCT/US2011/059889.
Marian Simo et al., "Adsorption/Desorption of Water and Ethanol on 3A Zeolite in Near-Adiabatic Fixed Bed", Ind. Eng. Chem. Res., 2009, 48, 9247-9260.
Hidetoshi Kita et al., "Synthesis of a zeolite NaA membrane for pervaporation of water/organic liquid mixtures", Journal of Materials Science Letters, 14 (1995) 206-208.
International Search Report and Written Opinion mailed Jul. 30, 2012 in corresponding International Application No. PCT/US2012/035189.
International Search Report and Written Opinion mailed Aug. 20, 2012 in corresponding International Application No. PCT/US2011/046498.
International Search Report and Written Opinion mailed Aug. 2, 2012 in corresponding International Application No. PCT/US2012/035220.
International Search Report and Written Opinion mailed Jul. 30, 2012 in corresponding International Application No. PCT/US2012/035273.
Tracy J. Benson et al., "Cellulose Based Adsorbent Materials for the Dehydration of Ethanol Using Thermal Swing Adsorption", Adsorption, vol. 11, 2005, pp. 697-701.
Yu Huang et al., "Low-Energy Distillation-Membrane Separation Process", Ind. Eng. Chem. Res., vol. 49, 2010, pp. 3760-3768.
International Search Report and Written Opinion mailed Aug. 6, 2012 in corresponding International Application No. PCT/US2012/035196.
Anonymous, "Studies in Extractive and Azeotropic Distillation Series; Study No. 4—Separation of Alcohols from the Acetate/Alcohol/Water Ternary by Extractive Distillation", May 9, 2008, XP 55033135, pp. 1-9.
V. Ragaini et al., "Increasing the value of dilute acetic acid streams through esterification Part I. Experimental analysis of the reaction zone", Applied Catalysis B: Environmental, vol. 64, 2006, pp. 66-71.
International Search Report and Written Opinion mailed Jul. 30, 2012 in corresponding International Application No. PCT/US2011/059891.
International Search Report and Written Opinion mailed Jul. 11, 2012 in corresponding International Application No. PCT/US2012/035203.
Yang et al, "Process of Ethanol Synthesis through esterification of acetic acid and economic analysis", No. 4, 2011, pp. 1-15.
S. Ordonez et al., "The role of metal and support sites on the hydrogenation of acetic acid on Ru-based catalysts", 21st NAM San Francisco, CA, Jun. 10, 2009.
Burkhanov et al., "Palladium-Based Alloy Membranes for Separation of High Purity Hydrogen from Hydrogen-Containing Gas Mixtures", Platinum Metals Rev., 2011, vol. 1, pp. 3-12.
N. Calvar et al., "Esterification of acetic acid with ethanol: Reaction kinetics and operation in a packed bed reactive distillation column", Chemical Engineering and Processing, 46 (2007) 1317-1323.
T. Yokoyama et al., "Carboxylic Acids and Derivatives", Fine Chemicals through Heterogenous Catalysis, pp. 370-379, 2001.

\* cited by examiner

US 8,895,786 B2

PROCESSES FOR INCREASING ALCOHOL PRODUCTION

FIELD OF THE INVENTION

The present invention relates generally to processes for producing alcohol and, in particular, to processes for increasing ethanol production by hydrolyzing ester contaminants contained in a crude ethanol product to form additional ethanol.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acetic acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

The need remains for improved processes for recovering ethanol from a crude product obtained by reducing alkanoic acids, such as acetic acid, and/or other carbonyl group-containing compounds. In addition, the need exists for reducing the amount of impurities, such as ester impurities, that are formed as byproducts of the hydrogenation reaction.

SUMMARY OF THE INVENTION

The present invention is directed to improved processes for recovering ethanol and for improved processes for reducing the amount of impurities, in particular ethyl acetate, formed in an acetic acid hydrogenation process. In a first embodiment, the present invention is directed to a process for producing ethanol, the process comprising the steps of: (a) hydrogenating acetic acid in a reactor in the presence of a catalyst to form a crude ethanol product; (b) separating at least a portion of the crude ethanol product in a first distillation column to yield a first distillate comprising ethanol and ethyl acetate and a first residue comprising acetic acid; and (c) separating at least a portion of the first distillate in a second distillation column to yield a second distillate comprising ethyl acetate and a side stream comprising ethanol. In one aspect, the process of the present invention further comprises the step of hydrolyzing a portion of the ethyl acetate in the first distillate to form ethanol and acetic acid. Step (c) may further comprise forming a second residue comprising acetic acid.

In a second embodiment, the present invention is directed to a process for producing ethanol, the process comprising the steps of: (a) hydrogenating acetic acid in a reactor in the presence of a catalyst to form a crude ethanol product; (b) separating at least a portion of the crude ethanol product in a first distillation column to yield a first distillate comprising ethanol and ethyl acetate and a first residue comprising acetic acid; (c) hydrolyzing at least a portion of the ethyl acetate under conditions effective to form additional ethanol and additional acetic acid; and (d) separating at least a portion of the first distillate in a second distillation column to yield a side stream comprising ethanol and a second residue comprising the residual acetic acid.

In a third embodiment, the present invention is directed to a process for producing ethanol, the process comprising the steps of: (a) hydrogenating acetic acid in a reactor in the presence of a catalyst to form a crude ethanol product; (b) separating at least a portion of the crude ethanol product in a first distillation column to yield a first distillate comprising ethanol, ethyl acetate and a minor amount of acetic acid and a first residue comprising acetic acid; (c) increasing the amount of ethanol and the amount of acetic acid in the first distillate; and (d) separating at least a portion of the first distillate in a second distillation column to yield a second distillate comprising ethyl acetate and a side stream comprising ethanol. In one aspect, step (d) further comprises forming a second residue comprising acetic acid.

In a fourth embodiment, the present invention is directed to a process for purifying a crude ethanol product comprising ethanol, ethyl acetate and acetic acid, the process comprising the steps of: (a) separating at least a portion of the crude ethanol product in a first distillation column to yield a first distillate comprising ethanol and ethyl acetate and a first residue comprising acetic acid; and (b) separating at least a portion of the first distillate in a second distillation column to yield a second distillate comprising ethyl acetate, a side stream comprising ethanol, and optionally a second residue comprising acetic acid. In one aspect, the process of the present invention further comprises hydrolyzing at least a portion of the ethyl acetate in the first distillate to form a hydrolyzed second distillate comprising ethanol and acetic acid prior to being separated in step (b).

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Figure 1:
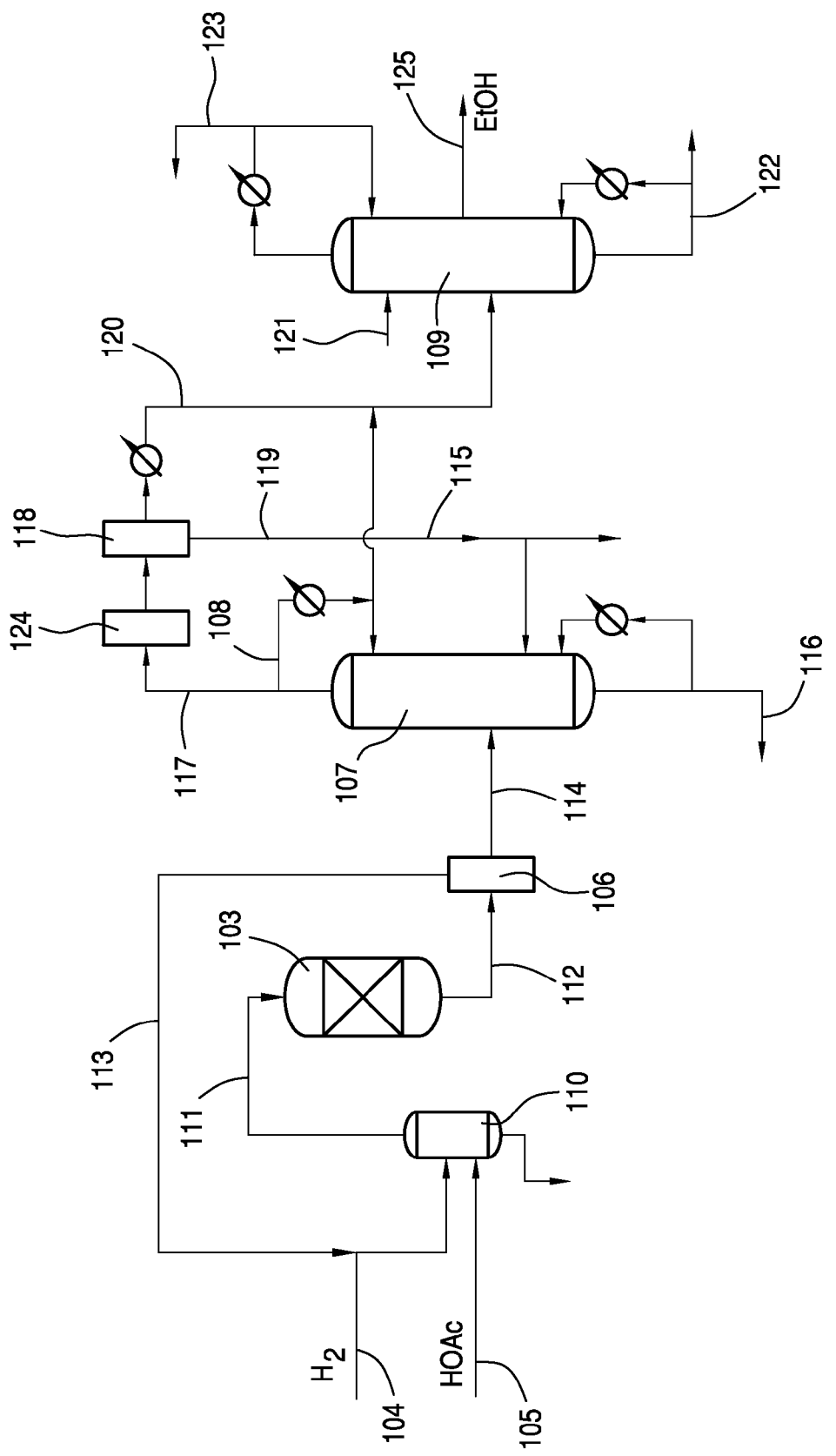
FIG. 1 is a schematic diagram of an ethanol production system with a hydrolysis unit and a water separator for removing water from the first distillate in accordance with one embodiment of the present invention.

The present invention relates to processes for recovering ethanol, optionally from a crude ethanol product produced by hydrogenating acetic acid in the presence of a catalyst. The crude ethanol product formed by the hydrogenation reaction may comprise ethanol, water, ethyl acetate, unreacted acetic acid, and other impurities. The concentration of some of these compounds in the reaction mixture is largely a factor of catalyst composition and process conditions. However, water concentration in the reaction mixture is not dictated by these factors because water is co-produced with ethanol in the hydrogenation reaction in about a 1:1 molar ratio. Thus, producing additional ethanol also results in the production of additional water.

In addition to water, a crude ethanol product formed from the hydrogenation of acetic acid typically contains ethyl acetate (EtOAc), which is formed along with water from the equilibrium reaction between ethanol (EtOH) and unreacted acetic acid (HOAc), as follows.

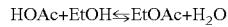

$$HOAc + EtOH \rightleftharpoons EtOAc + H_2O$$

Diethyl acetal (DEA) also may be formed with water from ethanol and acetaldehyde (AcH) according to the following reaction.

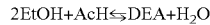

$$2EtOH + AcH \rightleftharpoons DEA + H_2O$$

The present invention advantageously reduces the amount of ethyl acetate and DEA in a crude ethanol product and provides a low energy separation scheme for recovering product ethanol. In a preferred embodiment, the process comprises the steps of: (a) hydrogenating acetic acid in a reactor in the presence of a catalyst to form a crude ethanol product; (b) separating at least a portion of the crude ethanol product in a first distillation column to yield a first distillate comprising ethanol, ethyl acetate and/or DEA and a first residue comprising acetic acid; and (c) separating at least a portion of the first distillate in a second distillation column to yield a second distillate comprising ethyl acetate, a side stream comprising ethanol and optionally a second residue comprising acetic acid and/or DEA. Preferably, the process further comprises the step of hydrolyzing a portion of the ethyl acetate in the first distillate to form ethanol and acetic acid thereby increasing overall selectivity to ethanol. Additionally or alternatively, the process further comprises the step of hydrolyzing a portion of the DEA in the first distillate to form ethanol and acetaldehyde.

Hydrogenation of Acetic Acid

The process of the present invention may be used with any hydrogenation process for producing ethanol or with any other process that forms a crude ethanol product, as defined herein. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and U.S. Pat. No. 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and U.S. Pat. No. 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydro-gasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 cm³/g as measured by mercury intrusion porosimetry and a packing density of about 0.352 g/cm³ (22 lb/ft³).

A preferred silica/alumina support material is KA-160 silica spheres from Sud Chemie having a nominal diameter of about 5 mm, a density of about 0.562 g/ml, an absorptivity of about 0.583 g H₂O/g support, a surface area of about 160 to 175 m²/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. No. 7,608,744 and U.S. Pat. No. 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | <90 | 0 to 50 | 15 to 70 | 20 to 70 |
| Water | 5 to 40 | 5 to 30 | 10 to 30 | 10 to 26 |
| Ethyl Acetate | <30 | <20 | 1 to 12 | 3 to 10 |
| Acetaldehyde | <10 | <3 | 0.1 to 3 | 0.2 to 2 |
| Others | 0.1 to 10 | 0.1 to 6 | 0.1 to 4 | — |

The amounts indicated as less than (<) in the tables throughout present specification are preferably not present and if present may be present in trace amounts or in amounts greater than 0.0001 wt. % up to the specified upper range limit.

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, for example, greater than 75%, e.g., greater than 85% or greater than 90%.

Hydrolysis and Ethanol Recovery

The ethanol recovery process begins with the introduction of the crude ethanol product into an initial separation column (first column), which separates the crude ethanol product into a distillate comprising ethanol, ethyl acetate, optionally DEA and water, and a residue comprising water and unreacted acetic acid. Preferably, a majority of the water from the crude ethanol product is separated into the residue of the first column (first residue), the conditions in the first column are such that a sufficient amount of water enters the first distillate for hydrolysis of the ethyl acetate and/or DEA. The amount of water in the first distillate preferably is provided in excess relative to the amount of ethyl acetate in the first distillate. In some preferred embodiments, the first distillate has a water: ethyl acetate molar ratio of greater than 1:1, greater than 2:1, greater than 3:1, greater than 5:1 or greater than 10:1. In some embodiments, additional water from within or outside of the reaction system may be added to the first distillate to provide the desired water:ethyl acetate ratio.

In theoretical embodiments where ethanol and water are the only products of the hydrogenation reaction, the crude ethanol product comprises 71.9 wt. % ethanol and 28.1 wt. % water. However, not all of the acetic acid fed to the hydrogenation reactor is typically converted to ethanol. Subsequent reactions of ethanol, such as esterification, may form other byproducts such as ethyl acetate. Hence, ethyl acetate is a byproduct that reduces the yield of ethanol of the process and increases the waste that must be taken out of the system. In accordance with a preferred embodiment of the invention, the distillate from the first column (first distillate) is directed, in whole or in part, to a hydrolysis unit in which ethyl acetate (and/or DEA) contained therein is hydrolyzed to form ethanol and acetic acid or ethanol and acetaldehyde, respectively.

The esterification reaction that produces ethyl acetate has a liquid phase equilibrium constant ($K_{est}$) equal to 4.0. (See, for example, Witzeman and Agreda in, "Acetic Acid and its Derivatives," Marcel Dekker, NY, 1992, p. 271, the entirety of which is incorporated herein by reference.) The hydrolysis of ethyl acetate has an equilibrium constant, $K_{hyd}$, of 0.25, which is the reciprocal of the $K_{est}$.

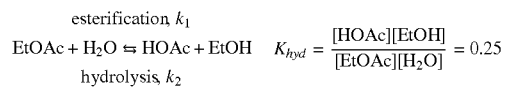

Until the excess acetic acid, which is not converted to products in the hydrogenation reactor, is substantially removed from the crude ethanol product, e.g., in an acid separation column, the composition favors esterification of ethanol with acetic acid to form ethyl acetate and water. In one embodiment of the present invention, substantially all of the excess acetic acid is removed. One or more derivative streams that are formed in the separation system may contain small amounts of acetic acid. As such, any mixture of ethanol, ethyl acetate and water in the derivative streams are not at chemical equilibrium, and the hydrolysis of ethyl acetate is thermodynamically favored.

In one embodiment, as discussed above, ethyl acetate (and/or DEA) in the first distillate is hydrolyzed to reduce the concentration thereof and form additional ethanol and acetic acid (or ethanol and acetaldehyde). The first distillate preferably comprises ethanol, ethyl acetate and water, wherein the water is present in an amount effective to hydrolyze the ethyl acetate. Optionally, additional water may be added to the first distillate as necessary to provide the desired water:ethyl acetate ratio. In addition, the first distillate preferably comprises substantially no acetic acid, e.g., less than 1 wt. % or less than 0.5 wt %, although it is contemplated that in some embodiments, it may be desirable to operate at increased water concentrations in the first distillate. Allowing more water to enter the first distillate results in increasing acetic acid carry over into the first distillate due to the difficulty in separating water from acetic acid. In any event, the first distillate preferably comprises no more than 3 wt. % acetic acid, or no more than 2 wt. % acetic acid.

Although ethyl acetate may be hydrolyzed in the absence of a catalyst, it is a preferred that a catalyst is employed to increase reaction rate. The hydrolysis of the ethyl acetate may be performed under liquid phase or gas phase conditions. In one embodiment, the hydrolysis of the ethyl acetate is performed continuously under liquid phase conditions.

According to one embodiment of the invention, the first distillate is passed through a hydrolysis unit comprising an ion exchange resin reactor bed. The ion exchange resin reactor bed may comprise a strongly acidic heterogeneous or homogenous catalyst, such as for example a Lewis acid, strongly acidic ion exchange catalyst, inorganic acids, and methanesulfonic acid. Exemplary catalysts include Amberlyst™ 15 (Rohm and Haas Company, Philadelphia, U.S.A.), Amberlyst™ 70, Dowex-M-31 (Dow Chemical Company), Dowex Monosphere M-31 (Dow Chemical Company), and Purolite CT type Catalysts (Purolite International SRL). The ion exchange resin reactor bed preferably is a gel or marco-reticular bed. Ion exchange resin reactor beds may be located externally to the distillation columns or within a distillation column. The outflow of the ion exchange resin reactor bed may be directly or indirectly returned to the separation system, preferably to a water removal unit or a second column, as discussed below. The hydrolysis step may occur in the liquid phase or in the vapor phase.

In one embodiment, the hydrolysis unit is included within the first column, while in other embodiments, the hydrolysis unit may be separate from the first column. Thus, the first column may comprise a hydrolyzing section, preferably in the upper portion of the first column or near the top of the first column. The hydrolyzing section may comprise an internal ion exchange resin reactor bed. In another embodiment, the hydrolyzing section is an enlarged portion of the first column, i.e., has a greater cross-sectional diameter than the lower half of the first column. This configuration may increase the residence time of the light boiling point materials in the column to facilitate further hydrolysis of ethyl acetate.

In one embodiment of the invention, other compounds may also be hydrolyzed with the ethyl acetate, such as diethyl acetal (DEA).

After the hydrolysis step, water is then optionally removed from the resulting stream to form an ethanol mixture stream, preferably comprising less than 10 wt. % water, less than 6 wt. % water or less than 4 wt. % water. In terms of ranges, the ethanol mixture stream may comprise from 0.001 to 10 wt. % water, e.g., from 0.01 to 6 wt. % water or from 0.1 to 4 wt. % water. Product ethanol is then recovered from the ethanol mixture stream.

The water removal step should be carefully selected since water and ethanol form an azeotrope that is difficult to separate in a distillation column. The ethanol-water azeotrope limits the recoverable ethanol in conventional distillation columns to an ethanol product comprising about 92-96 wt. % of ethanol. The energy required to approach this azeotrope in a distillation column, regardless of the presence of other compounds, is significant. The present invention involves using less energy in the first column than would be required to approach the azeotrope, resulting in some water being carried overhead in the first distillate. After hydrolyzing the ethyl acetate and/or DEA, residual water contained in the first distillate then may be removed from the distillate using a water separator, which beneficially requires less energy than is required for approaching the water/ethanol azeotrope in a distillation column. Thus, the present invention provides a low energy approach for (i) reducing ethyl acetate and/or DEA concentration in the first distillate, (ii) increasing overall ethanol selectivity, and (iii) dehydrating a crude ethanol product and thus removing water that is co-produced with ethanol.

The concentration of water in the first distillate after the hydrolysis step may vary depending on the acetic acid conversion and the amount of ethyl acetate contained in the first distillate prior to the hydrolysis step. In one embodiment, the first distillate comprises water in an amount greater than the amount of water in the ethanol/water azeotrope, e.g., in an amount greater than 4 wt. %, greater than 5 wt. %, or greater than 7 wt. %. In terms of ranges, the first distillate optionally comprises water in an amount from 4 wt. % to 38 wt. %, e.g., from 7 wt. % to 32 wt. %, or from 7 wt. % to 25 wt. %. As discussed above, the water preferably is present in an amount sufficient to hydrolyze the ethyl acetate and/or DEA contained in the first distillate, and preferably is present in the first distillate in an amount sufficient to provide a water:ethyl acetate molar ratio of greater than 1:1, greater than 2:1, greater than 3:1, greater than 5:1 or greater than 10:1.

Because the water concentration in the first distillate is typically greater than the acceptable amount of water for industrial or fuel grade ethanol applications, in one embodiment of the present invention, the process involves removing a substantial portion of the water from the first distillate, preferably after the hydrolysis step, to produce an ethanol mixture. Preferably, the water is removed before separating any appreciable amount of organics, e.g., acetaldehyde. In one embodiment, the water is removed prior to condensing the first distillate. For example, the first distillate in the vapor phase may be fed to an adsorption unit comprising a molecular sieve or a membrane. In some embodiments, the first distillate is condensed to a liquid and fed to a membrane. The heat of vaporization for water is provided to the first distillate to allow water to permeate through the membrane. In preferred embodiments, at least 50% of the water in the first distillate is removed, e.g., at least 60% of the water or at least 75% of the water, based on the total amount of water in the first distillate. In more preferred embodiments, from 90 to 99% of the water may be removed from the first distillate. Thus, the resulting ethanol mixture may comprise only a minor amount of water, from 0.01 to 10 wt. %, e.g., from 0.5 to 6 wt. %, or from 0.5 to 4 wt. %. In addition, since the ethyl acetate has been hydrolyzed, the resulting ethanol mixture also preferably comprises only a minor amount of ethyl acetate, e.g., from 0.1 to 50 wt. %, from 0.5 to 25 wt. % or from 1 to 15 wt. %. If the ethanol mixture contains DEA, it preferably comprises only a lower amount of DEA, e.g., from 10 wppm to 10000 wppm, from 25 to 5000 wppm or from 50 to 1500 wppm. In one embodiment, the ethanol mixture comprises a water concentration that is less than the amount of water in the ethanol/water azeotrope. In order to achieve a water concentration that is below the amount of water in the ethanol/water azeotrope, a large of amount of energy is required. Thus, the present invention beneficially removes water from the first distillate, after the hydrolysis step, to yield an ethanol mixture without using a large amount of energy. Also, because the ethanol mixture comprises less water, the need to remove water during later stages of product separation is also reduced.

The process of the present invention may use any suitable technique for removing water from the first distillate after the hydrolysis step. For example, water may be removed in the vapor phase, before condensation, or in the liquid phase. Water may be removed, for example, using an adsorption unit, membrane, molecular sieves, extractive column distillation, or a combination thereof. Suitable adsorption units include pressure swing adsorption (PSA) units and thermal swing adsorption (TSA) units. The adsorption units may comprises molecular sieves, such as aluminosilicate compounds.

A membrane or an array of membranes may also be employed to separate water from the distillate. The membrane or array of membranes may be selected from any suitable membrane that is capable of removing a permeate water stream from a stream that also comprises ethanol and ethyl acetate.

In an exemplary embodiment, the energy requirements of the first column in the process according to the present invention may be less than 5.5 MMBtu per ton of refined ethanol, e.g., less than 4.5 MMBtu per ton of refined ethanol or less than 3.5 MMBtu per ton of refined ethanol. In some embodiments, the process may operate with higher energy requirements provided that the total energy requirement is less than the energy required to remove most of the water from the crude ethanol product in the distillate, e.g., more than 65% of the water in the crude ethanol product.

The water that is removed from the first distillate after the hydrolysis step may be returned to the first column and ultimately removed from the first column via the first residue. In one embodiment, a portion of the removed water may be condensed and returned below the feed point of the crude ethanol product to the first column, e.g., near the bottom of the first column. Depending on the water removal technique, there may be some ethanol and ethyl acetate in the removed water and thus it may be desirable to recover these compounds by returning at least a portion of the removed water to the first column. Returning the removed water to the first column may increase the amount of water withdrawn as the residue. In other embodiments, a portion of the removed water may be fed to a separation column, e.g., a second column, preferably a second column, used in recovering an ethanol product from the ethanol mixture. The presence of a small amount of water, e.g., less than 10 wt. % water based on the total feed, in the second column may be beneficial in facilitating the separation of ethanol from other components, e.g., acetic acid (which may be made up of unreacted acetic acid and/or acetic acid formed from the hydrolysis of ethyl acetate), residual ethyl acetate or acetaldehyde, that may be present in the ethanol mixture. A portion of the removed water may also be purged as needed to remove water from the system.

In a preferred embodiment, the second column separates the ethanol product in a side stream, and removes acetic acid formed in the hydrolysis step via the residue (the second residue). In some embodiments, the ratio of ethanol separated in the side stream to ethanol separated in the second residue is from 100:1 to 1:10, e.g., from 50:1 to 1:5 or from 20:1 to 1:2. Any residual ethyl acetate and/or acetaldehyde (e.g., formed from the hydrolysis of DEA), may be removed in a second distillate of the second column.

The ethanol mixture that is formed after hydrolysis and preferably after the water removal step may enter the second column above or below where the product ethanol side stream exits the column. Feeding the ethanol mixture into the second column above the side stream, may result in acetic acid going into the ethanol product (side stream). Conversely, adding the ethanol mixture to the second column below the side stream may result in unreacted ethyl acetate going into the ethanol product.

All or a portion of the second distillate may be sent to the reactor or reaction zone for conversion thereof to additional ethanol. Similarly, all or a portion of the second residue, particularly the acetic acid in the second residue, may be sent to the reactor or reaction zone for additional ethanol formation. Additionally or alternatively, all or a portion of the second residue may be directed to the first column in which acetic acid may be recovered in the first residue.

The ethanol mixture may be further processed in the second column to recover product ethanol. In some embodiments, it may be desirable to maintain a concentration of water in the second column. Depending if a water separate is employed on the first distillate, and if so, the type of water separator, the ethanol mixture may comprise less than 0.5 wt.

% water. To control the water concentration, a by-pass line may be used to split the first distillate before or after the hydrolysis step, but preferably before the water removal step. The split ratio may vary to control the amount of water in the feed to the second column. In one embodiment, the split ratio may range from 10:1 to 1:10, e.g., from 5:1 to 1:5 or about 1:1. Other split ratios may be used when controlling the water concentration. The distillate in the by-pass line is not separated to remove water and may be combined or co-fed with the ethanol mixture to the second column. The combined distillate and ethanol mixture may have a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %. The additional water for the second column may be recovered in the second residue and/or in the ethanol side stream. As a result, it may be desired depending on the intended application to separate remaining water from the ethanol side stream.

Figure 2:
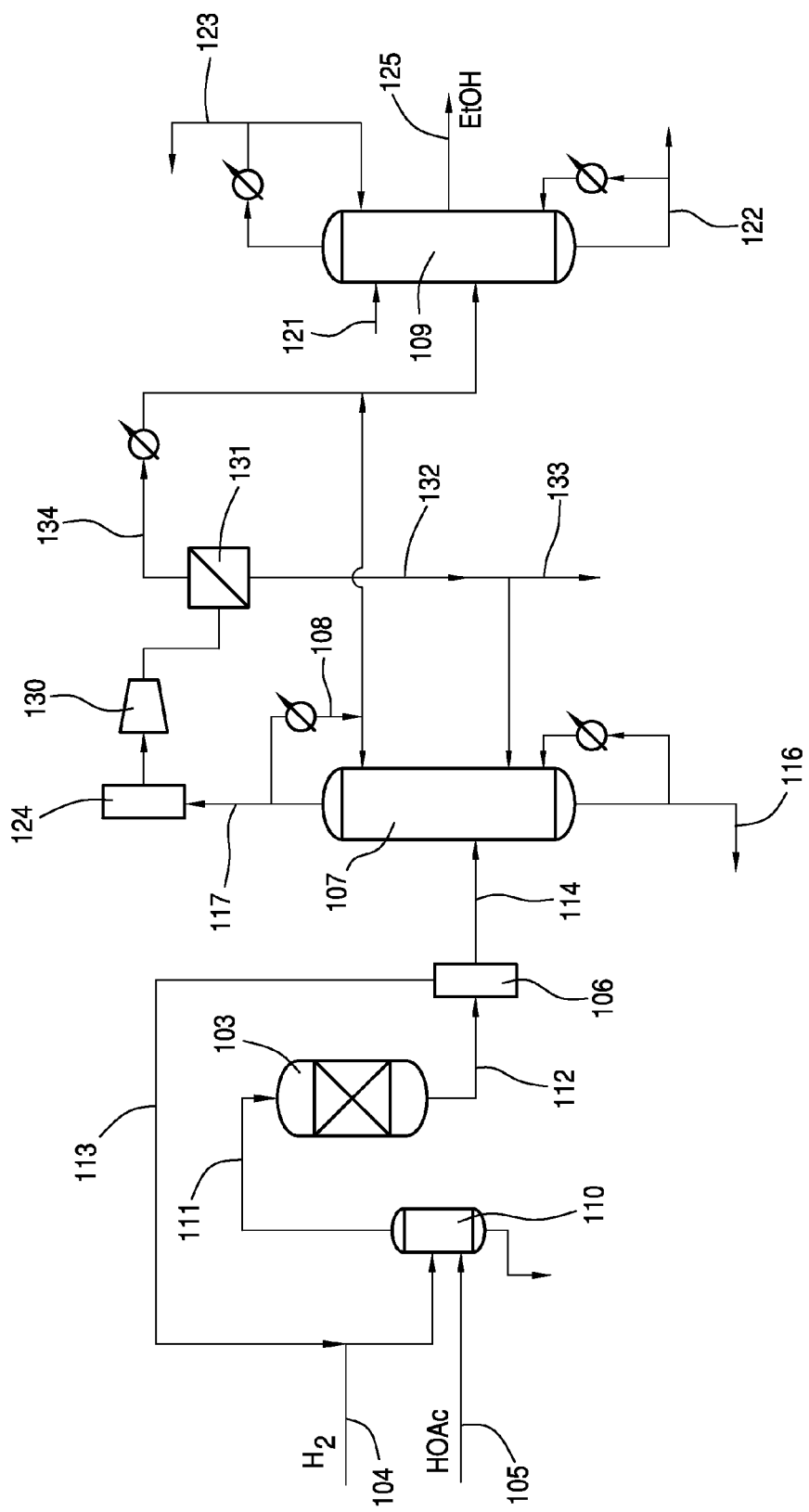
FIG. 2 is a schematic diagram of an ethanol production system with a hydrolysis unit and a membrane for removing water from the first distillate in accordance with one embodiment of the present invention.

Exemplary ethanol recovery systems in accordance with embodiments of the present invention are shown in FIGS. 1 and 2. System 100 comprises reaction zone 101 and separation zone 102. Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1, and may be recycled or discarded. In addition, although FIG. 1 shows line 111 being directed to the top of reactor 103, line 111 may be directed to the side, upper portion, or bottom of reactor 103. Further modifications and additional components to reaction zone 101 and separation zone 102 are described below.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 110, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 112.

The crude ethanol product stream in line 112 may be condensed and fed to a separator 106, which, in turn, provides a vapor stream 113 and a liquid stream 114. Suitable separators 106 include a flasher or a knockout pot. The separator 106 may operate at a temperature of from 20° C. to 250° C., e.g., from 30° C. to 225° C. or from 60° C. to 200° C. The pressure of separator 106 may be from 50 kPa to 2000 kPa, e.g., from 75 kPa to 1500 kPa or from 100 kPa to 1000 kPa. Optionally, the crude ethanol product in line 112 may pass through one or more membranes to separate hydrogen and/or other non-condensable gases.

The vapor stream 113 exiting separator 106 may comprise hydrogen and hydrocarbons, which may be purged and/or returned to reaction zone 101. As shown, vapor stream 113 is combined with the hydrogen feed 104 and co-fed to vaporizer 110. In some embodiments, the returned vapor stream 113 may be compressed before being combined with hydrogen feed 104.

The liquid stream 114 from separator 106 is withdrawn and pumped to the side of distillation column 107. In one embodiment, the contents of liquid stream 114 are substantially similar to the crude ethanol product obtained from the reactor in line 112, except that the composition has been depleted of hydrogen, carbon dioxide, methane and/or ethane, which are preferably removed by separator 106. Accordingly, liquid stream 114 may also be referred to as a crude ethanol product. Exemplary components of liquid stream 114 are provided in Table 2. It should be understood that liquid stream 114 may contain other components, not listed, such as components derived from the feed.

TABLE 2

COMPOSITION OF LIQUID STREAM 114

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 40 | 5 to 30 | 10 to 30 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 114, may comprise propanol, e.g., isopropanol and/or n-propanol, in an amount from 0.001 to 0.1 wt. %, from 0.001 to 0.05 wt. % or from 0.001 to 0.03 wt. %. It should be understood that these other components may be carried through in any of the distillate or residue streams described herein and will not be further described herein, unless indicated otherwise.

Optionally, crude ethanol product in line 112 or in liquid stream 114 may be further fed to an esterification reactor, hydrogenolysis reactor, or combination thereof. An esterification reactor may be used to consume acetic acid present in the crude ethanol product to further reduce the amount of acetic acid to be removed. Hydrogenolysis may be used to convert ethyl acetate in the crude ethanol product to ethanol in embodiments where a large amount of ethyl acetate is formed, although the need for a hydrogenolysis unit is mitigated by the use of a hydrolysis unit as described herein.

In the embodiment shown in FIG. 1, line 114 is introduced in the middle part of first column 107, e.g., second or third quarter. Depending on the composition of the crude ethanol product in line 114 and the operating conditions of first column 107, the first column 107 separates the crude ethanol product in line 114, preferably continuously, into a first distillate in line 117 and a first residue in line 116. In one embodiment, no entrainers are added to first column 107. The first distillate in line 117 comprises ethanol, other organics and water. The first residue in line 116 comprises unreacted acetic acid, water, and other heavy components, if present. In some embodiments, especially with higher conversions of acetic acid of at least 80%, or at least 90%, it may be beneficial to remove a substantial portion of the water, e.g. at least 35% to 90% of the water, from liquid stream 114, in the first residue along with substantially all the acetic acid.

When column 107 is operated under about 170 kPa, the temperature of the residue exiting in line 116 preferably is from 90° C. to 130° C., e.g., from 95° C. to 120° C. or from 100° C. to 115° C. The temperature of the distillate exiting in line 117 preferably is from 60° C. to 90° C., e.g., from 65° C. to 85° C. or from 70° C. to 80° C. In some embodiments, the pressure of first column 107 may range from 0.1 kPa to 510 kPa, e.g., from 1 kPa to 475 kPa or from 1 kPa to 375 kPa.

The first distillate in line 117 comprises water, as discussed above, in addition to ethanol and other organics, such as ethyl acetate and/or DEA. In terms of ranges, the concentration of water in the first distillate in line 117 preferably is from 4 wt. % to 38 wt. %, e.g., from 7 wt. % to 32 wt. %, or from 7 to 25 wt. %. As shown in FIG. 1, prior to condensing the first distillate in line 117, first distillate in line 117 is fed to a hydrolysis unit 124 in which ethyl acetate and water (preferably in excess) react to form ethanol and acetic acid. The hydrolysis unit may comprise, for example, an ion exchange material or other material for catalyzing the hydrolysis reaction, as described above. After hydrolysis, the resulting ethanol mixture is directed to a water separator 118 for removal of water. Water separator 118 may be an adsorption unit, membrane, molecular sieves, extractive column distillation, or a combination thereof.

In a preferred embodiment, water separator 118 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separator 118 may remove at least 95% of the water from the first distillate in line 117, and more preferably from 99% to 99.99% of the water from the first distillate, in a water stream 119. All or a portion of water stream 119 may be returned to column 107, where it preferably is ultimately recovered from column 107 in the first residue in line 116. Additionally or alternatively, all or a portion of water stream 119 may be purged via line 115. The remaining portion of first distillate 117 exits the water separator 118 as ethanol mixture stream 120. A portion of the first distillate in line 108 may be condensed and refluxed to first column 107, as shown, for example, at a ratio of from 10:1 to 1:100, e.g., from 2:1 to 1:50 or from 1:1 to 1:10. The reflux ratios may vary with the number of stages, feed locations, column efficiency and/or feed composition. Operating with a reflux ratio of greater than 3:1 may be less preferred because more energy may be required to operate the first column 107. Preferably, ethanol mixture stream 120 is not returned or refluxed to first column 107. Optionally, a portion of the first distillate in line 108 is directed to the second column 109, as shown, to provide a limited amount of water, thereby facilitating residual ethyl acetate separation from ethanol in the second column 109.

In another aspect, shown in FIG. 1, all or a portion of the water in water stream 119 is fed to first column 107 at a point below where the first distillate in line 108 is refluxed to first column 107.

Exemplary components of the first distillate (before hydrolysis) and ethanol mixture stream 120 (after hydrolysis and water removal) and first residue in line 116 are provided in Table 3 below. In a preferred embodiment, the first distillate initially comprises at least 0.5 wt. % ethyl acetate, e.g., at least 1 wt. % or at least 2 wt. % ethyl acetate, which may be hydrolyzed in the hydrolysis step. It should also be understood that these streams may also contain other components, not listed, such as components derived from the feed.

TABLE 3

FIRST COLUMN WITH HYDROLYSIS UNIT AND PSA

| | Conc. (wt. %) | Conc. (wt. %) | Conc. (wt. %) |
|---|---|---|---|
| First Distillate (before hydrolysis) | | | |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Ethanol Mixture (after hydrolysis and water removal) | | | |
| Ethanol | 20 to 95 | 30 to 95 | 40 to 95 |
| Water | <10 | 0.01 to 6 | 0.1 to 2 |
| Acetic Acid | <25 | 0.001 to 20 | 0.01 to 15 |
| Ethyl Acetate | <50 | <45 | <40 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| First Residue | | | |
| Acetic Acid | <90 | 1 to 50 | 2 to 35 |
| Water | 30 to 100 | 45 to 95 | 60 to 90 |
| Ethanol | <1 | <0.9 | <0.3 |

Some species, such as acetals, may decompose in first column 107 such that very low amounts, or even no detectable amounts, of acetals remain in the distillate or residue. In addition, an equilibrium reaction between acetic acid and ethanol or between ethyl acetate and water may occur in the crude ethanol product after it exits reactor 103. Depending on the concentration of acetic acid in the crude ethanol product, this equilibrium may be driven toward formation of ethyl acetate. This equilibrium may be regulated using the residence time and/or temperature of crude ethanol product as well as in hydrolysis unit 124.

Depending on the amount of water and acetic acid contained in the residue of first column 107, line 116 may be treated in one or more of the following processes. The following are exemplary processes for further treating first residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from first residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to reactor 103. The resulting water stream may be used as an extractive agent, for example to second column 109 via line 121 as discussed below, or to hydrolyze an ester-containing stream in a hydrolysis unit.

In other embodiments, for example where first residue in line 116 comprises less than 50 wt. % acetic acid, possible options include one or more of: (i) returning a portion of the residue to reactor 103, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery (WAR) distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue in line 116 comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the first residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in the waste water treatment facility.

Reverting to FIG. 1, ethanol mixture stream 120 is introduced to a second column 109, preferably in the top part of column 109, e.g., top half or top third. Second column 109 may be a tray column or packed column. In one embodiment, second column 109 is a tray column having from 5 to 70 trays, e.g., from 15 to 50 trays or from 20 to 45 trays. As one example, when a 30 tray column is utilized in a column without water extraction, ethanol mixture stream 120 is introduced at tray 2.

Optionally, the second column may be an extractive distillation column. Suitable extractive agents may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. In another aspect, the extractive agent may comprise water. If the extraction agent comprises water, the water may be obtained from an external source or from an internal return/recycle line from one or more of the other columns, such as the water stream 119. Generally, the extractive agent is fed above the entry point of ethanol mixture stream 120, as shown by optional line 121. When extractive agents are used, a suitable recovery system, such as a further distillation column, may be used to remove the extractive agent and recycle the extractive agent if desired.

Second column 109 is operated to separate ethanol mixture stream 120 or a portion thereof into a second distillate in line 123, side stream 125 comprising ethanol product, and a second residue in line 122. Second distillate in line 123 may comprise, for example, ethyl acetate and acetaldehyde, while second residue comprises acetic acid formed in the hydrolysis of the ethyl acetate. Second residue may be sent in whole or in part to the reactor for conversion to additional ethanol or sent to the first column as discussed above. Side stream 125 comprises ethanol and, which optionally is a salable finished ethanol product. If water is added to the second column 109, some water may be contained in second residue 122 and/or side stream 125, which may require an additional water removal step depending on the intended application for the ethanol product.

Although the temperature and pressure of second column 109 may vary, when at about 20 kPa to 70 kPa, the temperature of the second residue exiting in line 122 preferably is from 30° C. to 75° C., e.g., from 35° C. to 70° C. or from 40° C. to 65° C. The temperature of the second distillate exiting in line 123 preferably is from 20° C. to 55° C., e.g., from 25° C. to 50° C. or from 30° C. to 45° C. The temperature of the side draw stream 125 preferably is from 30° C. to 75° C., e.g., from 35° C. to 70° C. or from 40° C. to 65° C. Second column 109 may operate at a reduced pressure, near or at vacuum conditions, to further favor separation of ethyl acetate and ethanol. In other embodiments, the pressure of second column 109 may range from 0.1 kPa to 510 kPa, e.g., from 1 kPa to 475 kPa or from 1 kPa to 375 kPa. Exemplary distillate, side draw and residue compositions for second column 109 are provided in Table 4, below. It should be understood that the second distillate, side stream and second residue may also contain other components, not listed, such as components in the feed.

TABLE 4

| SECOND COLUMN | | | |
|---|---|---|---|
| | Conc. (wt. %) | Conc. (wt. %) | Conc. (wt. %) |
| Second Distillate | | | |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Side Stream | | | |
| Ethanol | 50 to 99 | 60 to 99 | 70 to 99 |
| Water | <15 | 0.01 to 10 | 0.1 to 8 |
| Ethyl Acetate | 0.01 to 1 | 0.05 to 0.75 | 0.1 to 0.5 |
| Acetic Acid | <0.5 | <0.01 | 0.001 to 0.01 |
| Second Residue | | | |
| Ethanol | 50 to 99 | 60 to 90 | 65 to 85 |
| Water | <20 | 0.001 to 15 | 0.01 to 10 |
| Ethyl Acetate | <1 | 0.001 to 2 | 0.001 to 0.5 |
| Acetic Acid | <15 | <10 | 0.1 to 5 |

The weight ratio of ethanol in the side draw to ethanol in the second distillate preferably is at least 2:1, e.g., at least 5:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1.

Second distillate in line 123, which comprises ethyl acetate and/or acetaldehyde, preferably is refluxed as shown in FIG. 1, for example, at a reflux ratio of from 1:30 to 30:1, e.g., from 1:15 to 15:1 or from 1:5 to 5:1. In one aspect, the second distillate in line 123 or a portion thereof may be returned reactor 103. For example, it may be advantageous to return a portion of second distillate 123 to reactor 103. The ethyl acetate and/or acetaldehyde in the second distillate may be further reacted in hydrogenation reactor 103 or in a secondary reactor. The outflow from the secondary reactor may be fed to reactor 103 to produce additional ethanol or to a distillation column, such as columns, 107, 115, or 118, to recover additional ethanol.

In the embodiment shown in FIG. 1, the finished ethanol product produced by the process of the present invention may be taken from the side stream in line 125. Advantageously, the finished ethanol product may be recovered using water separator and two columns according to the present invention. The finished ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 5.

TABLE 5

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

In another embodiment of the present invention, as shown in FIG. 2, the first distillate in line 117 from first column 107 passes to a hydrolysis unit 124 to convert ethyl acetate and/or DEA to ethanol and acetic acid or ethanol and acetaldehyde, respectively. The resulting stream is passed through a compressor 130 and is fed to a membrane 131. Membrane 131 preferably operates in the vapor phase. The water in the first distillate in line 117 permeates across the membrane 131 to form a permeate stream 132. Permeate stream 132 may comprise at least 80% of the water from the first distillate, and more preferably at least 90% of the water. In one embodiment, permeate stream 132 also comprises less than 10% of the ethanol from the first distillate, e.g., less than 5% of the ethanol. A portion of permeate stream 132 may be returned to column 107, preferably below the feed point of the liquid stream 114. A portion of permeate stream 132 may be purged from the system, as shown by line 133, to control the amount of water in column 107.

The portion of distillate that does not cross membrane 131 forms retentate stream 134, e.g., an ethanol mixture stream, and is fed to second column 109 as described above in FIG. 1. In one embodiment, retentate stream 134 comprises more water than shown in the ethanol mixture stream compositions provided in Table 3. For example, retentate stream 134 may comprise from 0 to 10 wt. % water, and more preferably form 0 to 5 wt. % water. The additional water present in retentate stream 134 may be beneficial in separating ethyl acetate and ethanol in second column 109. The additional water that is fed to second column 109 preferably is removed with the second residue in line 122 and/or in the side stream 125 and may necessitate a secondary dewatering step, as discussed above, to provide an ethanol product having the desired water concentration.

Although one membrane is shown in FIG. 2, it should be understood that a suitable array of membranes may also be used.

Figure 3:
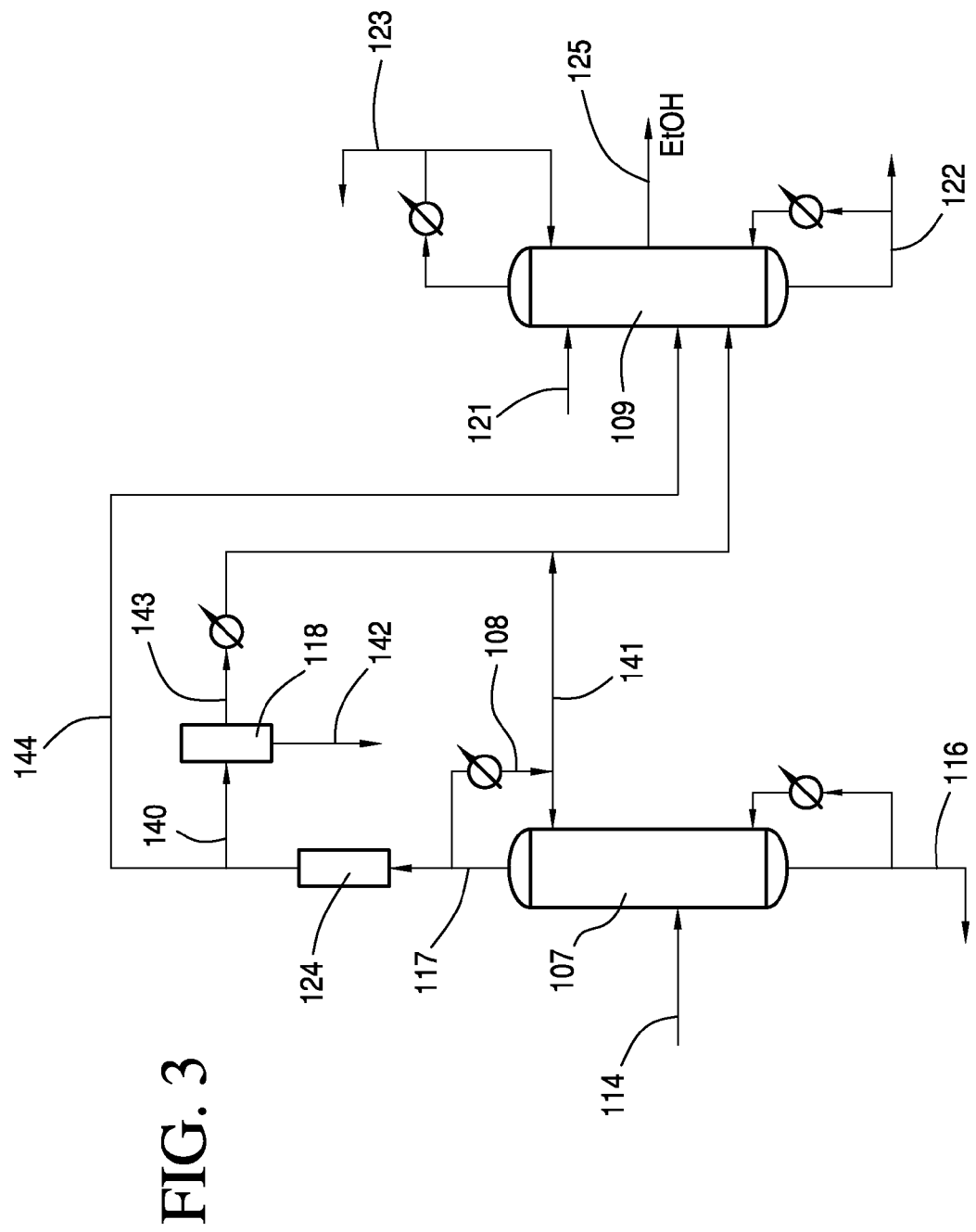
FIG. 3 is a schematic diagram of a water separator for removing water from the first distillate in accordance with one embodiment of the present invention.

In most embodiments of the present invention, it is desirable to remove water from the first distillate as shown in FIGS. 1 and 2. In FIG. 3, the first distillate in line 117, after passing through hydrolysis unit 124, is split into a main line 140 and a hydrolyzed bypass line 144. In one embodiment, the split ratio may range from 10:1 to 1:10, e.g., from 5:1 to 1:5 or about 1:1. Main line 140 is fed to water separator 118 to produce a water stream 142 and an ethanol mixture stream 143, while hydrolyzed bypass line 144 is directed to second column 109. All or a portion of water stream 142 may be returned to first column 107 as described above in FIGS. 1 and 2. A portion of first distillate in line 117 may be condensed and refluxed to first column 107 via line 108, e.g., at a reflux ratio from 10:1 to 1:100, e.g., from 2:1 to 1:50 or from 1:1 to 1:10. An additional bypass line 141 may be taken from the reflux line 108 and fed directly to second column 109 along with ethanol mixture stream 143 and/or hydrolyzed bypass line 144. Flow control valves (not shown) may be used to control the split between the main line 140, hydrolyzed bypass line 144 and additional bypass line 141 such that a desired water concentration is fed to the second column 109. In one embodiment, a portion of bypass line 141 is refluxed to first column 107, as shown. In another embodiment, bypass line 141 is not refluxed to first column 107 and a separate reflux line (not shown) may be provided. A portion of bypass line 141 may be condensed and separately fed to second column 109 with all or a portion of ethanol mixture stream 143.

The separation of the first distillate 117 into main line 140 and bypass lines 141 and 144 may be controlled based on the desired combined concentration of water of streams 141, 143, 144. In an embodiment, bypass line 141 contains a higher concentration of water than the ethanol mixture stream 143 and hydrolyzed bypass stream 144. The combined water concentration of streams 141, 143, 144 optionally is greater than 0.5 wt. %, e.g., greater than 2 wt. % or greater than 5 wt. %. In terms of ranges, the total water concentration of streams 141, 143, 144 may be from 0.5 to 15 wt. %, e.g., from 2 to 12 wt. %, or from 5 to 10 wt. %. The water content in bypass line 141 may be beneficial for the separation of ethanol and ethyl acetate in distillation column 109. In another embodiment, additional water may be added to column 109 via line 121. Optionally, portions of the water in water stream 142 may be added to column 109.

Each of the columns shown in FIGS. 1-3 may be selected from any distillation column capable of performing the specified separation and/or purification step. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order. Similarly, the modifiers "first" and "second" when used to refer to distillation columns should be understood as being used to distinguish the reactors rather than requiring that they be the first or second column, respectively, in the separation system. It is contemplated, for example, that a crude reaction product may be sent from a reactor or flash unit to an initial separation unite, e.g., distillation column, that forms a crude ethanol product that is then sent for processing in the first and second columns of the present invention.

The associated condensers and liquid separation vessels that may be employed with each of the distillation columns may be of any conventional design and are simplified in the figures. Heat may be supplied to the base of each column or to a circulating bottoms stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, the process comprising the steps of:
   (a) hydrogenating acetic acid in a reactor in the presence of a catalyst to form a crude ethanol product;
   (b) separating at least a portion of the crude ethanol product in a first distillation column to yield a first distillate comprising ethanol, at least 0.1 wt. % water, and ethyl acetate and a first residue comprising acetic acid;
   (c) hydrolyzing a portion of the ethyl acetate in the first distillate to form ethanol and acetic acid; and
   (d) separating at least a portion of the hydrolyzed first distillate in a second distillation column to yield a second distillate comprising ethyl acetate and a side stream comprising from 10 wt. % to 99.5 wt. % ethanol, less than 1.0 wt. % ethyl acetate, and less than 1.0 wt. % acetic acid, and a second residue comprising acetic acid;
   wherein the first distillate, prior to hydrolysis, has a water to ethyl acetate molar ratio of greater than 3:1.

2. The process of claim 1, wherein the ratio of ethanol in the side stream to ethanol in the second residue is from 100:1 to 1:10.

3. The process of claim 1, further comprising the step of recycling at least a portion of the acetic acid from the second residue to the reactor.

4. The process of claim 1, further comprising the step of recycling at least a portion of the acetic acid from the second residue to the first distillation column.

5. The process of claim 1, further comprising introducing a water stream to the first distillate.

6. The process of claim 1, wherein the hydrolyzing occurs in an ion exchange bed.

7. The process of claim 6, wherein the ion exchange bed is external from the first distillation column and between the first distillation column and the second distillation column.

8. The process of claim 1, wherein the first distillate initially comprises at least 0.5 wt. % ethyl acetate.

9. The process of claim 1, wherein the first distillate initially comprises at least 1 wt. % ethyl acetate.

10. The process of claim 1, wherein the first distillate initially comprises less than 2 wt. % acetic acid.

11. The process of claim 1, wherein at least 95% of acetic acid fed to the first distillation column is separated into the first residue.

12. The process of claim 1, wherein from 30 to 90% of the water fed to the first distillation column is separated into the first residue.

13. The process of claim 1, further comprising the step of recycling at least a portion of the ethyl acetate from the second distillate to the reactor.

14. The process of claim 1, further comprising the step of recycling at least a portion of the ethyl acetate from the second distillate to the first distillation column.

15. The process of claim 1, further comprising the step of removing water from at least a portion of the first distillate.

16. The process of claim 15, wherein the first distillate comprises less than 10 wt. % water after the water removal step.

17. The process of claim 15, wherein the water is removed from the first distillate using an adsorption unit, membrane, extractive distillation column, molecular sieve, or a combination thereof.

18. The process of claim 15, wherein the water is removed from the first distillate using a pressure swing adsorption unit or a thermal swing adsorption unit.

19. The process of claim 15, wherein a portion of the removed water is added to the second distillation column.

20. The process of claim 15, further comprising the step of adding water to the second distillation column under conditions effective to hydrolyze ethyl acetate contained therein and form additional ethanol and acetic acid.

21. The process of claim 1, wherein at least 10% of the ethanol fed to the second column is recovered in the side stream.

22. The process of claim 1, wherein the first distillation column is operated at a pressure from 6.9 to 68.9 kPaa.

23. The process of claim 1, wherein acetic acid conversion in the reactor is at least 90%.

24. The process of claim 1, wherein the first distillate is fed to the second column below the side stream.

25. A process for producing ethanol, the process comprising the steps of:
(a) hydrogenating acetic acid in a reactor in the presence of a catalyst to form a crude ethanol product;
(b) separating at least a portion of the crude ethanol product in a first distillation column to yield a first distillate comprising ethanol, at least 0.1 wt. % water, and ethyl acetate and a first residue comprising acetic acid;
(c) hydrolyzing at least a portion of the ethyl acetate under conditions effective to form additional ethanol and additional acetic acid; and
(d) separating at least a portion of the first distillate in a second distillation column to yield a side stream comprising from 10 wt. % to 99.5 wt. % ethanol, less than 1.0 wt. % ethyl acetate, and less than 1.0 wt. % acetic acid, and a second residue comprising acetic acid, wherein the second residue is returned to the reactor in step (a);
and wherein the first distillate, prior to hydrolysis, has a water to ethyl acetate molar ratio of greater than 3:1.

26. A process for producing ethanol, the process comprising the steps of:
(a) hydrogenating acetic acid in a reactor in the presence of a catalyst to form a crude ethanol product;
(b) separating at least a portion of the crude ethanol product in a first distillation column to yield a first distillate comprising ethanol, at least 0.1 wt. % water, ethyl acetate and a minor amount of acetic acid and a first residue comprising acetic acid;
(c) increasing the amount of ethanol and the amount of acetic acid in the first distillate; and
(d) separating at least a portion of the first distillate in a second distillation column to yield a second distillate comprising ethyl acetate and a side stream comprising from 10 wt. % to 99.5 wt. % ethanol, less than 1.0 wt. % ethyl acetate, and less than 1.0 wt. % acetic acid, and a second residue comprising acetic acid;
and wherein the first distillate in step (b) has a water to ethyl acetate molar ratio of greater than 3:1.

27. The process of claim 26, wherein water is added to the first distillate under conditions effective to hydrolyze ethyl acetate contained therein and form ethanol and acetic acid.

28. The process of claim 26, wherein the amount of acetic acid is increased by at least 0.1%.

29. The process of claim 26, wherein the amount of ethanol is increased by at least 0.1%.

* * * * *